United States Patent [19]
Taheri

[11] Patent Number: 5,824,064
[45] Date of Patent: Oct. 20, 1998

[54] TECHNIQUE FOR AORTIC VALVE REPLACEMENT WITH SIMULTANEOUS AORTIC ARCH GRAFT INSERTION AND APPARATUS THEREFOR

[76] Inventor: Syde A. Taheri, 268 Dan Troy, Williamsville, N.Y. 14221

[21] Appl. No.: 752,336

[22] Filed: Nov. 19, 1996

Related U.S. Application Data

[63] Continuation-in-part of Ser. No. 435,851, May 5, 1995, abandoned.

[51] Int. Cl.$^6$ .................................. A61F 2/06; A61F 2/24
[52] U.S. Cl. ................................... 623/2; 623/1; 606/108
[58] Field of Search ....................... 623/2, 1, 12; 600/36; 606/108, 198

[56] References Cited

U.S. PATENT DOCUMENTS 5,489,295  2/1996  Piplani et al. ............................. 623/1
5,571,172  11/1996  Chin ............................................ 623/1

*Primary Examiner*—David H. Willse
*Attorney, Agent, or Firm*—Lieberman & Nowak, LLP

[57] ABSTRACT

Transfemoral aortic valve replacement with the simultaneous insertion of an aortic arch graft, referred to as "TAVAG", is effected with a device comprising the following components: a U-shaped collapsible nitinol ring which is attached to a bioprosthetic valve, a thin walled predetermined graft with branches, a perforated self-expandable carrier capsule having a large slit therein, diamond shaped guide wires, and a ring to control opening and closing of the carrier capsule. The graft and valve are pulled up from the left femoral artery toward the aortic arch by pulling on the guide wires which are threaded through catheters inserted in each of the bilateral carotid and subclavian arteries toward the left femoral artery. Cerebral circulation is also maintained from the right femoral artery through a novel balloon catheter placed inside the carotid artery.

7 Claims, 6 Drawing Sheets

TECHNIQUE FOR AORTIC VALVE REPLACEMENT WITH SIMULTANEOUS AORTIC ARCH GRAFT INSERTION AND APPARATUS THEREFOR

CROSS REFERENCE TO RELATED APPLICATION

This invention is a continuation-in-part of prior application Ser. No. 08/435,851, filed on May 5, 1995 to the same inventor and is hereby expressly abandoned.

FIELD OF THE INVENTION

This invention relates to a technique for repairing aortic dissection and in particular for the simultaneous insertion of an aortic valve and aortic graft in a patient's ascending aorta, and to apparatus employed therefor.

BACKGROUND OF THE INVENTION

Heretofore, surgical techniques commonly employed for aortic arch aneurysm, particularly dissection of the thoracic aortic artery in response to aortic valve insufficiency have evidenced a high incidence of mortality. This has been attributed to the complexity of the surgical procedure involved, the need for a multiplicity of blood transfusions and post operative complications. Accordingly studies have continued in the search for new methods designed to obviate the foregoing limitations and to enhance the current technology.

In accordance with the present invention, this end has been successfully attained by a novel technique using a procedure involving the use of a stented endovascular graft which provides patients with an aortic arch graft with its branches simultaneously with the replacement of a bioprosthetic aortic valve.

SUMMARY OF THE INVENTION

Transfemoral aortic valve replacement with the simultaneous insertion of an aortic arch graft, referred to as "TAVAG", is effected with a device comprising the following components: a U-shaped collapsible nitinol ring which is attached to a bioprosthetic valve, a thin walled predetermined graft with branches, a perforated self-expandable carrier capsule having a large slit therein, diamond shaped guide wires, and a ring to control opening and closing of the carrier capsule. The graft and valve are pulled up from the left femoral artery toward the aortic arch by pulling on the guide wires which are threaded through catheters inserted in each of the bilateral carotid and subclavian arteries toward the left femoral artery. Cerebral circulation is also maintained from the right femoral artery through a novel balloon catheter placed inside the carotid artery.

BRIEF DESCRIPTION OF THE DRAWING

The invention will be more fully understood by reference to the following detailed description taken in conjunction with the accompanying drawing wherein.

DETAILED DESCRIPTION OF INVENTION

Figure 1B:
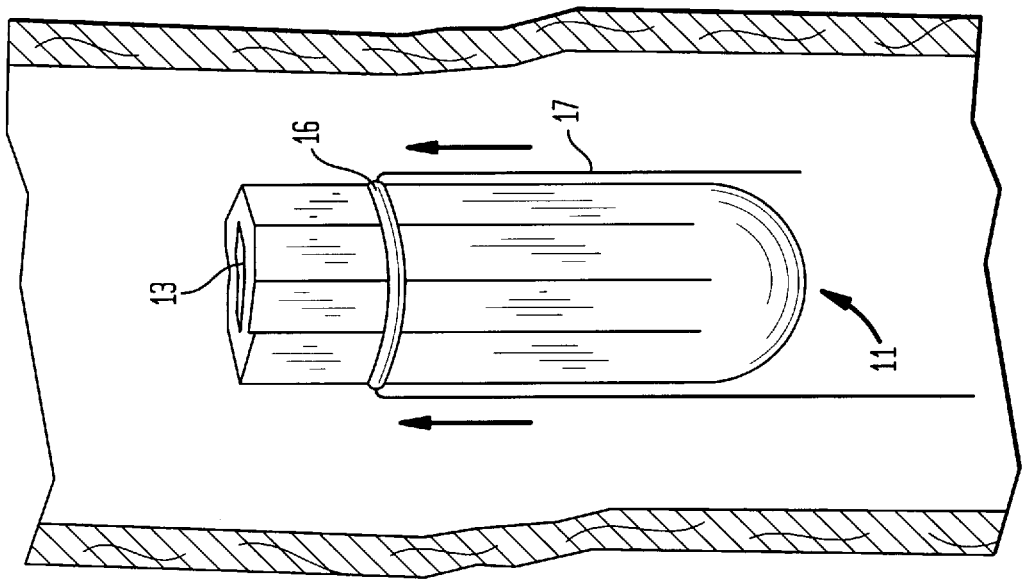
FIG. 1(b) is a front elevational view of the capsule shown in FIG. 1 in the closed position.
Figure 1A:
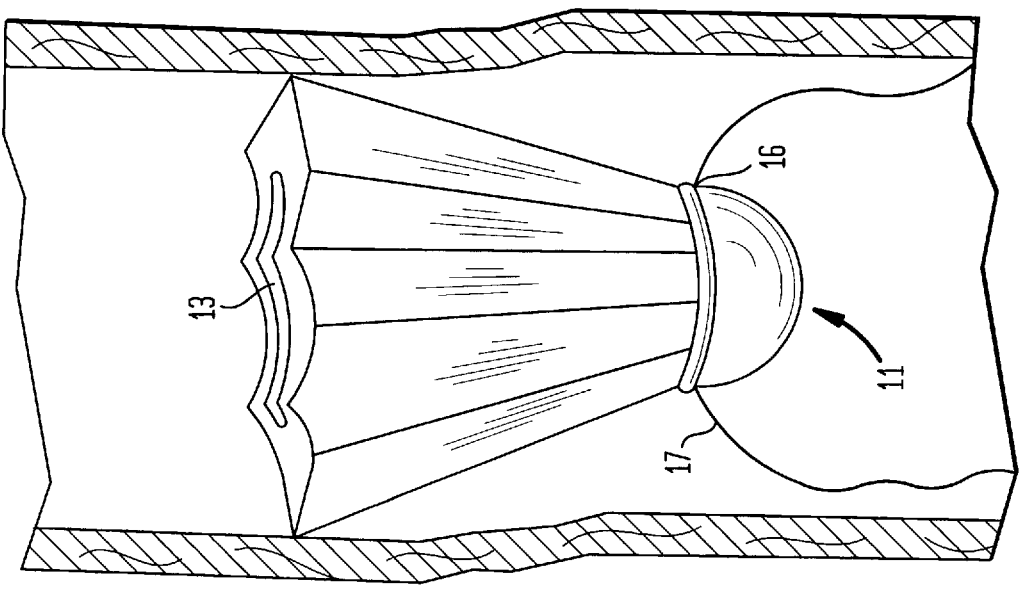
FIG. 1(a) is a front elevational view of a self-expandable carrier capsule of variable size and length, in the open position, adapted with a large slit for branches of a prosthetic graft.

With reference now more particularly to FIG. 1, there is shown a capsule 11 of variable size and length having an opening 13 through which branches of a prosthetic graft will extend. Opening and closing of capsule 11 is effected by motion of ring 16 which is effected by pulling and pushing on guide wire 17, or other mechanical means. FIG. 1(a) depicts capsule 11 in the open position and FIG. 1(b) depicts capsule 11 in the closed position.

Figure 2A:
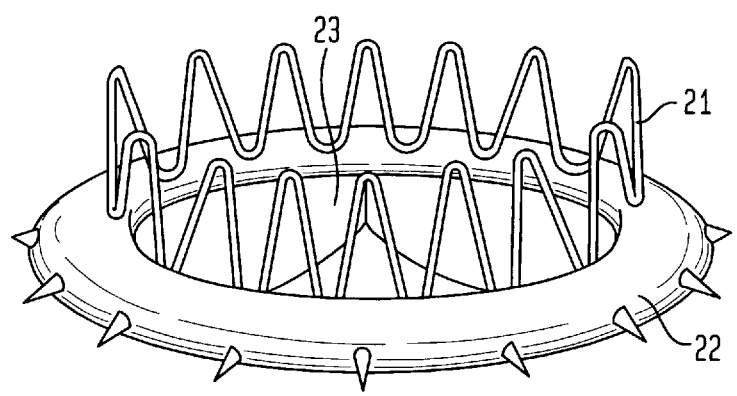
FIG. 2(a) is a frontal view in perspective of a U-shaped collapsible metal frame sewn to a prosthesis which is in turn sewn to a collapsible bioprosthetic valve or a xenograft valve.
Figure 2B:
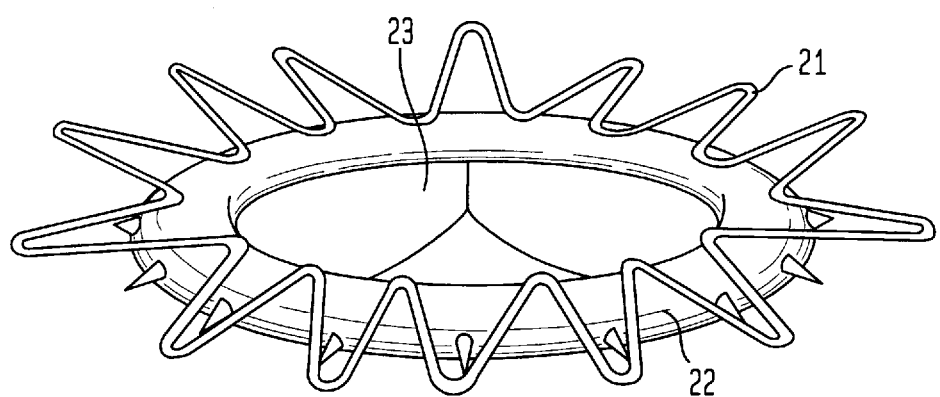
FIG. 2(b) is a frontal view of the structure of FIG. 2(a) in the closed position.

FIG. 2(a) is a frontal view in perspective of a collapsible interconnected multiple U-shaped metal frame in the open position comprising a stainless steel or nitinol thin wire U-shaped metal frame 21, typically 2 mm in diameter and 15 mm in length, sewn to a prosthesis 22 comprising either DACRON or GORTEX, both of which are brands of resilient polyester textile fibers. Frame 21 is sewn to a collapsible valve 23 which may be a bioprosthetic or a xenograft valve. FIG. 2(b) depicts the structure of FIG. 2(a) in the closed position.

Figure 3:
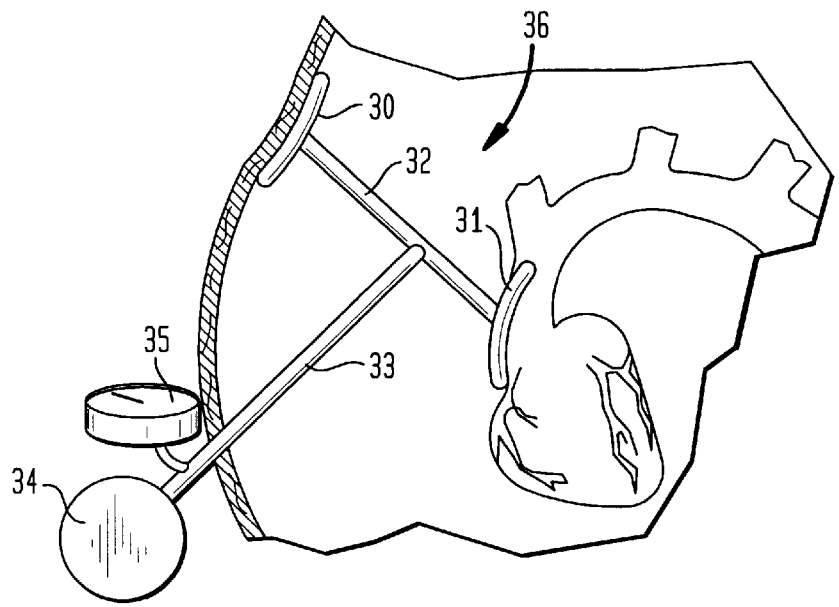
FIG. 3 is a front elevational view of a pressure controlled paddle shaped inflatable bar or external stent employed in the practice of the present invention.

With reference now to FIG. 3, a frontal view of a human chest cavity showing the use of an external stent in accordance with the invention is depicted. This device is similar to pillars in the front of a dwelling home. The device includes two large cushions 30 and 31 which cushion or paddle the ascending arch of the aorta. The cushions are connected by means of a semi rigid tubing 32 to which is connected tubing 33. The device is pressurized and controlled by an outside bulb 34 which inflates the cushions and which has a pressure control valve or gauge 35 to maintain the stent pressure at a level equal to the systemic pressure. The stent is inserted via the thoracoscopy approach in the thoracic cavity 36 via a chest port and thoracoscopy visualization. The device is directed to the pleural cavity and cushions are directed toward the ascending aorta and chest wall where they will be inflated to systemic pressure. Cushions 30 and 31 typically comprise silicone rubber. Tubing 32 is a hollow column tubing is semi rigid and may range from 30 to 35 cm. in length and from 8–12 mm. in width.

Figure 4A:
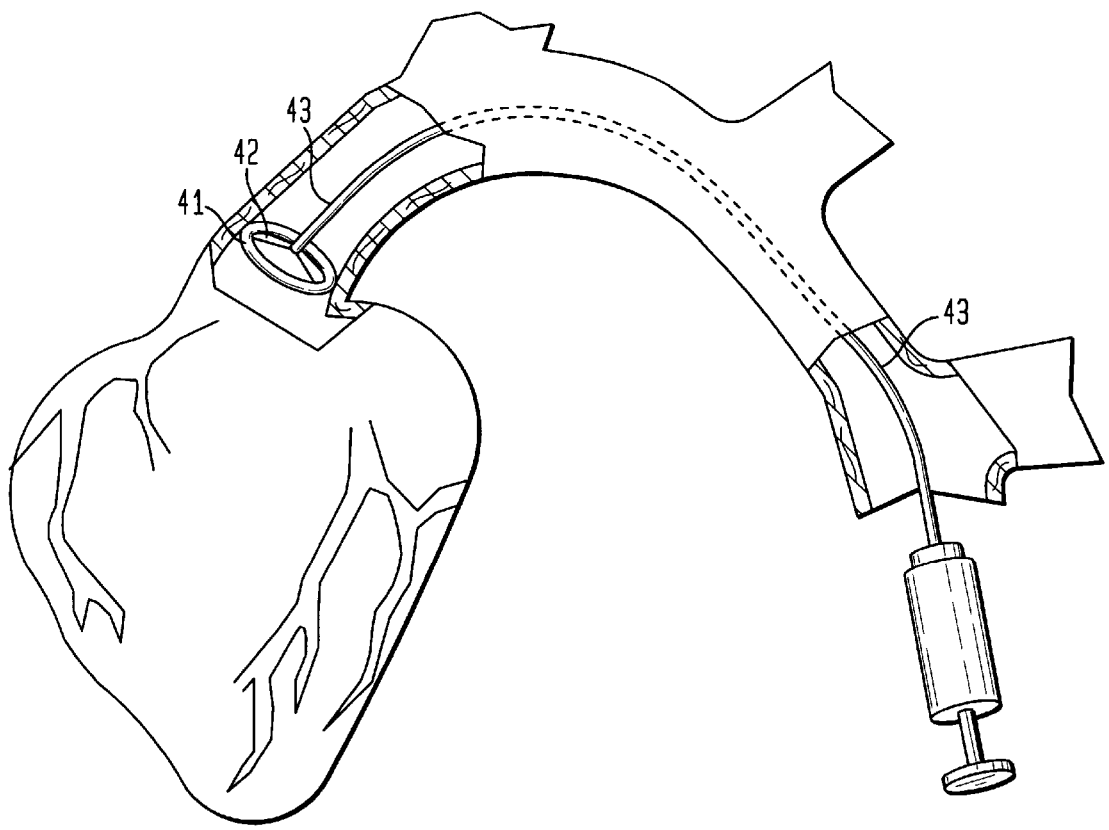
FIG. 4(a) is a frontal view in perspective of a pressure controlled internal single donut shaped stent employed in the practice of the present invention.
Figure 4B:
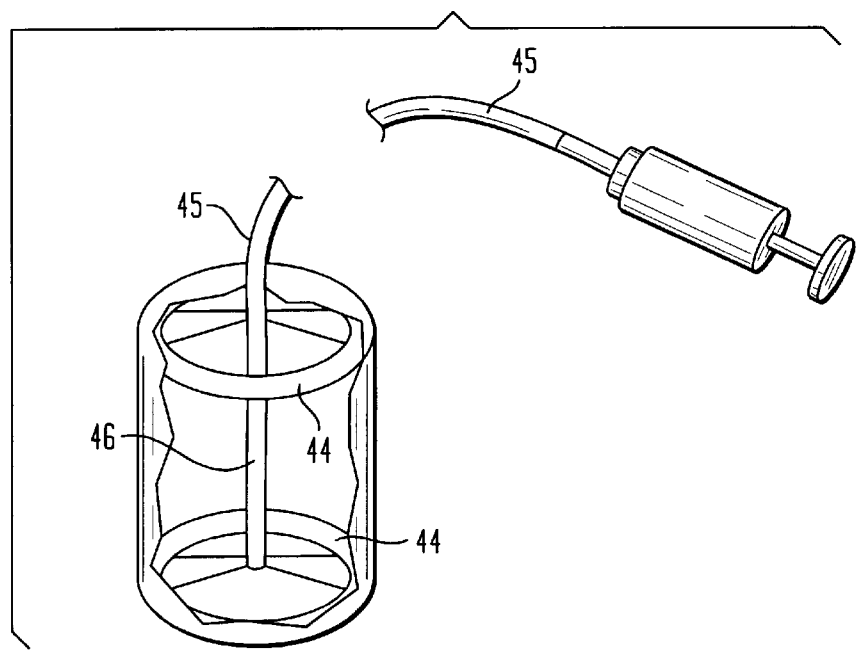
FIG. 4(b) is a frontal view in perspective of a pressure controlled internal double donut shaped stent employed in the practice of the present invention.

FIG. 4(a) is a frontal view in perspective of an internal stent in accordance with the invention. This figure shows a single or donut shaped balloon 41 which is connected by a silicone tube 42 to the shaft of a catheter 43. FIG. 4(b) shows a single or double donut shaped balloon 44 which is connected to a catheter 45 by means of silicone cylinder 46, typically 20–30 mm. in width and 1.0–1.5 cm. in height. The internal stent is inserted into the aorta via the femoral artery and lodged in the predetermined dissected site of the ascending aorta by inflating the donut shaped balloon against the torn aorta wall with the simultaneous outside pressure from the external stent, thereby preventing bleeding through the dissected point.

Figure 5:
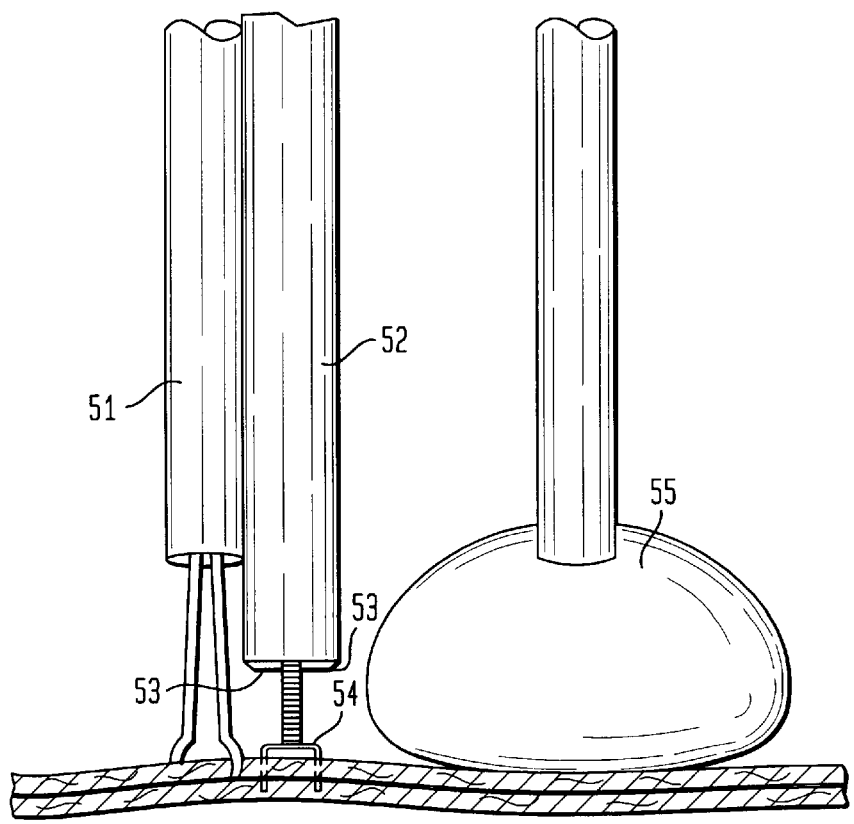
FIG. 5 is a frontal view of a double lumen guide wire stapling catheter employed in the practice of the present invention.

FIG. 5 is a frontal view of a double lumen guide wire stapling catheter employed in the practice of the present invention. Shown in the figure is a guide wire lumen 51, stapling carrying lumen 52 comprising a rectangular shaped tubing having a track 53 on each side thereof to allow a staple 54 to move downward to a desired location in a blood vessel. Plunger 55 is used to dislodge the staple at the conclusion of surgery. This device may also be used as an intervascular angiography catheter.

Figure 6:
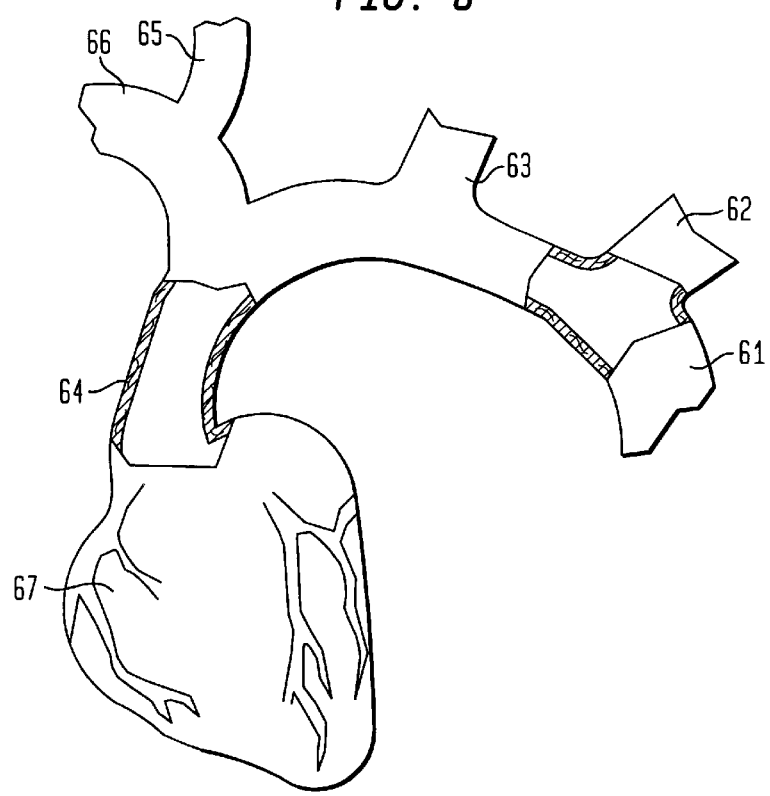
FIG. 6 is a frontal view of the anatomy of an aortic arch.

FIG. 6 is a frontal view of the anatomy of an aortic arch. Shown in the figure is femoral artery 61, left subclavian artery 62, left common carotid artery 63, ascending aorta 64, right carotid artery 65, right subclavian artery 66 and heart 67. In the practice of the invention, the graft of interest is brought from the femoral artery 61 in the groin to the arch of the aorta 64. This end is attained by means of a guide wire originating in a designated location in the subclavian arteries or carotid arteries which is directed toward the groin and passed through the respective branch of a graft to be inserted in that artery and returned via the same catheter to the subclavian region by pulling the guide wire. This permits the surgeon to bring the graft and the collapsible valve, if any, from the groin to the ascending aorta. Following intervascular graft suturing or stenting to a designated artery, the guide wire and balloon catheter are removed and the arteriotomy is closed.

Figure 7A:
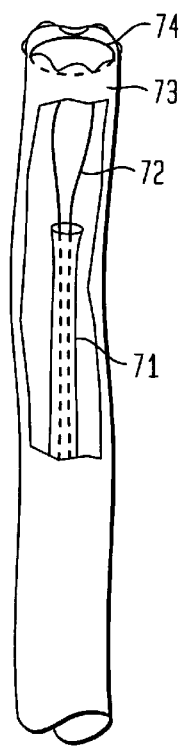
FIG. 7(a) is a frontal view in perspective of a purse string guide wire or suture prior to activation of the purse string.
Figure 7B:
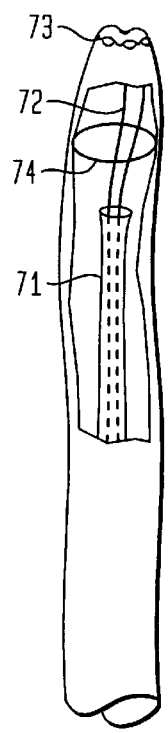
FIG. 7(b) is a frontal view in perspective of the device of FIG. 7(a) after activation of the purse string.

FIG. 7(a) is a frontal view in perspective of a purse string guide wire or suture prior to activation of the purse string which is suitable for use in the practice of the present invention. This device is a retriever and includes catheter 71 having guide wire 72 disposed therein and passing therethrough, guide wire 72 being attached to a purse string guide wire or suture 73 having a proximal ring 74 at the top end thereof. As the guide wire is pulled down, the proximal ring is approximated and separated from the aortic wall, thereby permitting the surgeon to retrieve or place it in a different location under direct observation utilizing an angioscope. FIG. 7(b) is a frontal view in perspective of the device of FIG. 7(a) after activation of the purse string.

Figure 8:
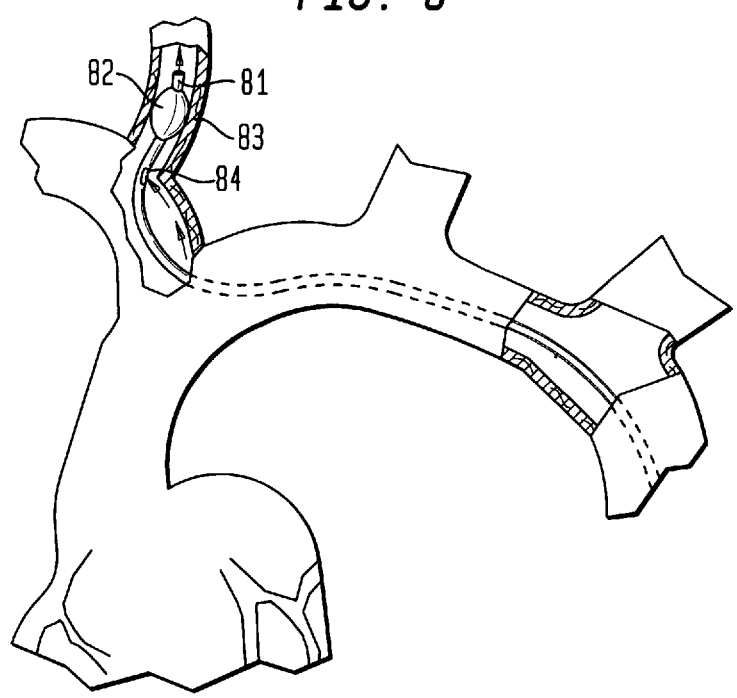
FIG. 8 is a frontal view, in perspective of a shunting catheter which provides cerebral circulation during a surgical procedure.

FIG. 8 is a frontal view, in perspective, of a shunting catheter for providing cerebral circulation during surgery. Shown in this FIG. is a balloon shunting catheter 81 including balloon 82 inserted internally in carotid artery 83. Also shown is an aperture 84 disposed within catheter 81 for supplying blood to the patient's brain during the surgical procedure. The catheter draws blood to the patient's brain from the patient's right femoral artery, and blocks off blood flow through the carotid artery while the surgeon operates in that region to repair an aneurysm. Use of this balloon catheter obviates the need for an external mechanical means for providing circulation to the patient's brain.

The present invention is described in terms of its preferred embodiments. However, it will be understood that these embodiments are set forth for purposes of exposition only and are not to be construed as limiting. The numbering sequence employed in referencing device elements is consistent in each figure.

The invention will be further described by reference to a typical exemplary embodiment in which a patient afflicted with an aortic aneurysm with or without an aortic valve insufficiency, is treated with the placement of a graft, and an aortic valve when appropriate. Depending on where the location of the aneurysm, the graft will have branches corresponding to the right and left, subclavian and carotid arteries. The first step in the surgical event involves exposing and dissecting the bilateral subclavian, carotid and left femoral arteries of the patient. Each of the dissected arteries is individually catheterized toward the left femoral artery. A guide wire is inserted in each of the catheters and directed toward the distal end of the catheters which have been placed inside the opening of the left femoral artery. In one preferred embodiment the guide wires are diamond tipped so as to allow easier passage through the graft. Each of the guide wires are passed through the respective branches of the prosthetic aortic graft and tied down to the graft. In one embodiment the guide wires are tied to threads which extend from the branches of the graft. The distal end of the guide wires are brought back through their respective catheters to the previously dissected artery and outside the patient's incision.

The graft is placed within a capsule of the type shown in FIGS. 1(a) and 1(b). The capsule has a ring 16 which is attached to some mechanical means including a stiff guide wire for opening and closing the capsule. In one preferred embodiment the capsule is placed within the open left femoral artery with its opening facing the patient's head and two stiff guide wires attached to ring 16 trailing outside the incised femoral artery. The capsule is closed by pushing on the stiff guide wires and raised toward the aorta by pulling on the guide wires passing through the graft. At the aorta the graft is released from the capsule by pulling on the stiff guide wires thereby opening the capsule. By gently pulling on the guide wires passing through the branches of the graft, the graft is directed to the respective branches of the aorta. At this point, an arch arteriogram is performed and the guide wires and catheters are removed. The side branches of the graft are then sutured, or by endovascular stenting techniques are secured in place, and lastly, the arteriotomy and skin incisions are closed.

Oftentimes, patient's with aortic aneurysms also suffer from aortic valve insufficiency. Consequently, it is often desirable to replace the aortic valve when repairing an aortic aneurysm. The method of the present invention as described above can be advantageously employed, together with a novel prosthetic aortic valve described below, to simultaneously repair an aortic aneurysm and replace an insufficient aortic valve. The valve used in accordance with the present invention is a collapsible interconnected multiple U-shaped metal frame comprised of stainless steel or nitinol thin wire and sewn to a bioprosthetic or a xenograft valve, typically 20 mm to 30 mm in diameter, 1 mm to 10 mm in length and 3 mm to 4 mm in thickness. The valve is sewn to the prosthetic graft used to repair the aortic aneurysm. The valve is introduced into the patient and maneuvered into place together with the prosthetic graft. During the procedure however, prior to maneuvering the graft into place, a fiber optic laser is introduced into the right subclavian artery to pulverize the existing damaged aortic valve. Thereafter, the prosthetic aortic valve is released from the expandable capsule by proximal pulling of the ring structure shown in FIG. 1, and secured to the ascending aorta wall.

When one of the branches of the graft corresponds with a carotid artery, one preferred embodiment of the present invention establishes carotid artery circulation with an internal carotid shunt or a double lumen shunting balloon catheter of the type shown in FIG. 8, as previously explained.

In the case of an unstable patient, it is preferred to place a percutaneous transaortic stent in the ascending aorta prior to any arterial exposure. In one advantageous embodiment of the present invention, a transaortic stent balloon catheter as shown in FIG. 4b, is placed at the site of the dissection within the aorta. The internal stent is donut shaped and connected to a silicone cylinder 20–30 mm wide and 10–15 cm long. It is inserted into the aorta via the femoral artery and lodged in the dissected site of the ascending aorta. By inflating the donut shaped balloon against the torn aorta wall from within the aorta and exerting outside pressure from an external stent as shown in FIG. 4, bleeding through the aneurysm is prevented.

The described technique is a novel concept which provides a safe and practical approach to a complex disorder. The technique reverses abnormal hemodynamics to normal circulation and by utilizing an aortic arch graft bypasses the dissected thoracic aorta. Consequently, this obviates the need for further dissection and establishes distal circulation to a predissected condition. Experience has revealed that this type of surgical procedure will successfully result in saving the lives of many thousands of patients from this disease.

It will be understood by those skilled in the art that variations may be made without departing from the spirit and scope of the invention. Thus, for example, the collapsible valve employed herein may be either a human valve (bioprosthetic) or an animal valve (xenograft) and the material comprising the U-shaped collapsible frame may be stainless steel or nitinol thin wire.

Additionally, it may be expedient to employ an intervascular twister in the practice of the present invention. This device which is unique may be introduced into a blood vessel from a distant location to seize a graft and twist it to yield either a large graft or a small graft of limited diameter. This permits the surgeon to pass into small arteries or affords the opportunity to seize the proximal part of a graft and twist it to push it forward toward the aortic arch.

What is claimed is:

1. A method for repairing an aortic aneurysm in a patient, with a prosthetic aortic graft, said prosthetic aortic graft having one or more branches corresponding to one or more of the left subclavian, right subclavian and carotid arteries, one branch corresponding to one artery, said method comprising the steps of:

exposing and dissecting one or more of said left subclavian, right subclavian and left carotid and right carotid arteries, and said patient's left femoral artery;

catheterizing each of said exposed subclavian and carotid arteries;

a first threading of a first end of a guide wire through each of said catheters in each of said exposed subclavian and carotid arteries toward and through said exposed, dissected femoral artery, each of said catheters having a different guide wire threaded therethrough, while maintaining a second end of each of said guide wires at said exposed, dissected subclavian and carotid arteries;

the second threading of each of said first ends of said guide wires through the branch in said prosthetic aortic graft and back through the catheter toward said exposed, dissected subclavian and carotid arteries corresponding to the artery through which said guide wire was first threaded, while anchoring each of said guide wires to their respective branches;

placing said prosthetic aortic graft into an openable and closeable capsule;

drawing said prosthetic aortic graft in said capsule from said femoral artery toward said patient's aortic arch by pulling on said first and second ends of said guide wires;

aligning each of said branches of said prosthetic aortic graft with said corresponding artery by pulling on the appropriate one of said guide wires;

securing said prosthetic aortic graft to said patient's aortic wall;

removing said catheters and guide wires; and closing and covering said dissected, exposed arteries.

2. A method according to claim 1 wherein said securing step includes suturing said prosthetic aortic graft to said patient's aortic wall.

3. A method according to claim 1 wherein said securing step includes stenting.

4. A method according to claim 1 wherein aortic valve replacement is to be performed simultaneously with the repairing of the aortic aneurysm, further comprising the steps of:

securing a prosthetic aortic valve to said prosthetic graft;

pulverizing said patient's aortic valve prior to securing said graft to said patient's aortic wall; and securing said prosthetic aortic valve and said prosthetic graft to said patient's aortic wall, simultaneously.

5. A method in accordance with claim 1 wherein said prosthesis comprises a material selected from the group consisting of DACRON and GORTEX.

6. A method according to claim 1 further comprising the steps of:

inserting an external stent in the thoracic cavity via a chest port, said external stent having first and second cushions separated by a semi-rigid tubing therebetween and an inflator tube connected at one end inside the thoracic cavity to said semi-rigid tube and connected at an opposite end outside said thoracic cavity to a bulb and gauge for inflating said cushions to the systemic pressure;

inflating said external stent;

inserting an internal stent through a femoral artery, said internal stent having an inflatable donut shaped balloon which is connected by a silicone tube to a shaft of a catheter lodging said internal stent at an aortic dissection; and inflating said donut shaped balloon against the aortic dissection from within the aortic arch and directly opposite to the external stent.

7. A method in accordance with claim 6 wherein the prosthetic aortic valve is selected from the group consisting of bioprosthetic valves and xenograft valves.

* * * * *